United States Patent [19]

Tamura et al.

[11] 4,202,968
[45] May 13, 1980

[54] NEW TUNICAMINE DERIVATIVES AND THEIR PREPARATION

[75] Inventors: Gakuzo Tamura, Tokyo; Akira Takatsuki, Ichikawa, both of Japan

[73] Assignee: Meiji Seika Kaisha, Ltd., Tokyo, Japan

[21] Appl. No.: 920,448

[22] Filed: Jun. 29, 1978

[30] Foreign Application Priority Data

Jul. 6, 1977 [JP] Japan ................... 52-79819

[51] Int. Cl.$^2$ ........................... C07H 17/00
[52] U.S. Cl. ................... 536/23; 536/17 R; 424/180
[58] Field of Search ................... 536/23, 17

[56] References Cited

FOREIGN PATENT DOCUMENTS 7329156  7/1970  Japan ......................... 536/23

OTHER PUBLICATIONS

Omura, S., J. of Antibiotics, 27(2), 1974, pp. 147-149.

*Primary Examiner*—Johnnie R. Brown
*Assistant Examiner*—Blondel Hazel
*Attorney, Agent, or Firm*—Haight & Huard

[57] ABSTRACT

New tunicamine derivatives are provided which exhibit antiviral activity against some virus, particularly Newcastle disease virus, and inhibitory activity against coccidiosis and which are also of particular value as intermediates for the preparation of a variety of useful antibacterial, antitumor and antiviral compounds. They have a structure of the formula:

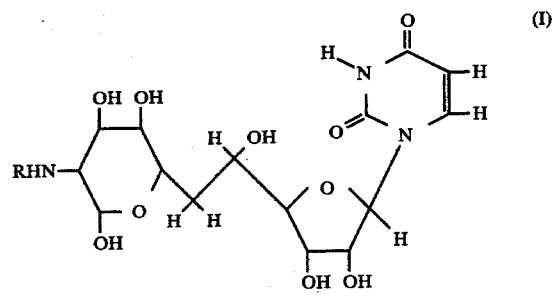

wherein R represents hydrogen or a fatty acid residue of the formula $(CH_3)_2CH(CH_2)_nCH=CHCO-$ where n represents an integer of 8 to 11 inclusive. They are prepared either by fermentation methods or by acid hydrolysis of the known antibiotic tunicamycin.

3 Claims, 4 Drawing Figures

NEW TUNICAMINE DERIVATIVES AND THEIR PREPARATION

BACKGROUND OF THE INVENTION

This invention relates to new and useful tunicamine derivatives and the preparation thereof.

We already provided in our Japanese Patent Publication No. 29156/73 a new anitibiotic substance, tunicamycin, and its preparation, which exhibits high antiviral and anitbacterial activities and is useful for treatment and protection against a variety of viral infections such as those caused by Newcastle disease virus (NDV), influenza virus and tobacco-mosaic virus and of bacterial infections such as those caused by the genera Bacillus, Candida, Microbacterium, etc. Tunicamycin is produced and isolated from cultivation of a tunicamycin-producing strain of the genus Streptomyces, e.g. *Streptomyces lysosuperificus*, in a nutrient medium under aerobic conditions as shown in the above-mentioned publication and has a chemical structure, which we have now confirmed, of the formula:

wherein n represents integers of 8 to 11 inclusive. As shown in the formula above, tunicamycin contains, as its structural units, uracil, fatty acid, N-acetylglucosamine and an anomalous $C_{11}$-aminodeoxy-dialdose. The last-mentioned $C_{11}$-aminodeoxy-dialdose, which is attached to an uracil residue, is a new sugar and we now designate the new sugar of the following formula as tunicamine.

BRIEF SUMMARY OF THE INVENTION

We have now found that new tunicamine derivatives as hereinafter defined are produced in a culture broth of the tunicamycin-producing strain of Streptomyces above-mentioned and successfully isolated and confirmed the said derivatives as new and useful compounds.

According to a first aspect of this invention, therefore, there are provided new tunicamine derivatives of the general formula:

wherein R represents hydrogen or a fatty acid residue of the formula $(CH_3)_2CH(CH_2)_nCH=CHCO-$ where n represents an integer of 8 to 11 inclusive.

For convenience's sake, the tunicamine derivative of formula (I) wherein R represents hydrogen is now designated as tunicamine derivative C, whereas the tunicamine derivatives of formula (I) wherein R represents fatty acid residues of the formula $(CH_3)_2CH(CH_2)_nCH=CHCO-$ where n represents integers of 8 to 11 inclusive, which are in the form of a mixture, are collectively designated as tunicamine derivative B.

DETALIED DESCRIPTION OF THE INVENTION

We have also found that the tunicamine derivatives of formula (I) according to this invention exhibit rather weak antibacterial activity, but have a significant antiviral activity against some virus, particularly Newcastle disease virus (NDV), and a significant inhibitory activity against coccidiosis caused in domestic fowls. The tunicamine derivatives of formula (I) are also of particular value as intermediates for the preparation of a variety of antibacterial, antitumor and antiviral agents.

Physical and chemical characterisitics of the tunicamine derivatives B and C which we have found are shown in Table 1.

Table 1

|  | Tunicamine derivative B | Tunicamine derivative C |
| --- | --- | --- |
| Melting point (°C.) | 228–230 (decomp.) | 185–187 (decomp.) |
| Specific optical rotation $[\alpha]_D^{20}$ | +12.6°(c=0.45, pyridine) | +29°(c=1.8, water) |
| Silica gel-thin layer chromatography | $R_f$ 0.65 single spot (butanol: acetic acid:water =4:1:1) | $R_f$ 0.41 single spot (butanol: acetic acid:water =2:1:) |
| Elemental analysis | C 56.87% H 8.08% N 6.51% O 27.18% | C36.88% H 5.79% N 8.27% O 33.12% |

Table 1-continued

|  | Tunicamine derivative B | Tunicamine derivative C |
|---|---|---|
| Molecular formula | $C_{29-32}H_{47-53}N_3O_{11}$ | $C_{15}H_{23}N_3O_{10}$ |
| Molecular weight | 613–655 | 405 |
| UV absorption spectrum | $\lambda max^{259}$nm (MeOH) $E^{1\%}_{1cm}$ 170 | $\lambda max^{261}$nm($H_2O$) $E^{1\%}_{1cm}$ 207 |

Figure 1:
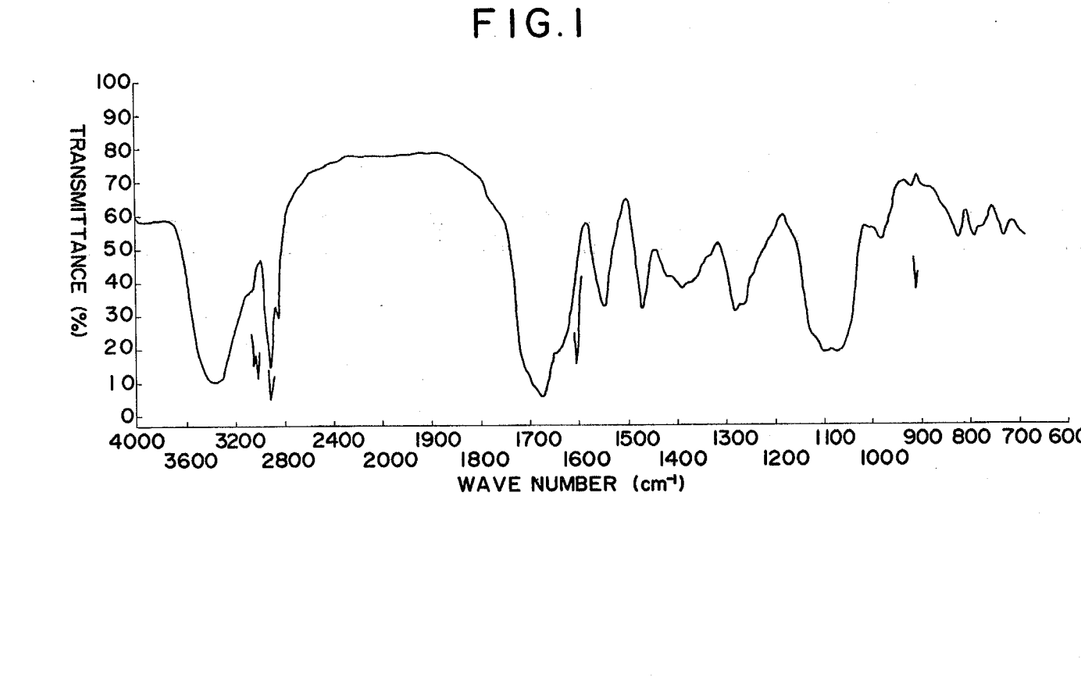
FIG. 1 shows a curve of the infrared absorption specturm of a sample of tunicamine derivative B pelleted in a KBr tablet.
Figure 2:
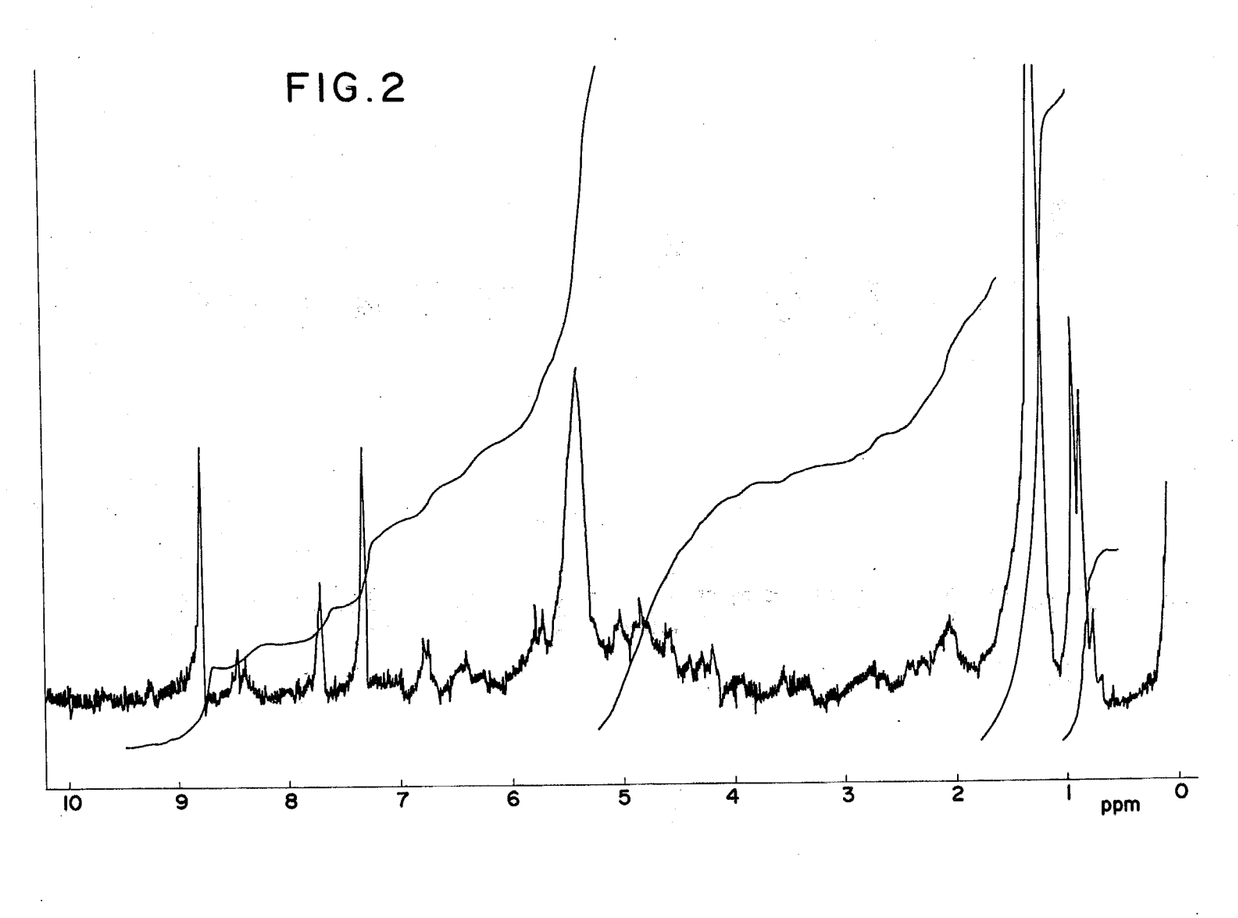
FIG. 2 shows a curve of the nuclear magnetic resonance spectrum of a sample of tunicamine derivative B in deuteropyridine.
Figure 3:
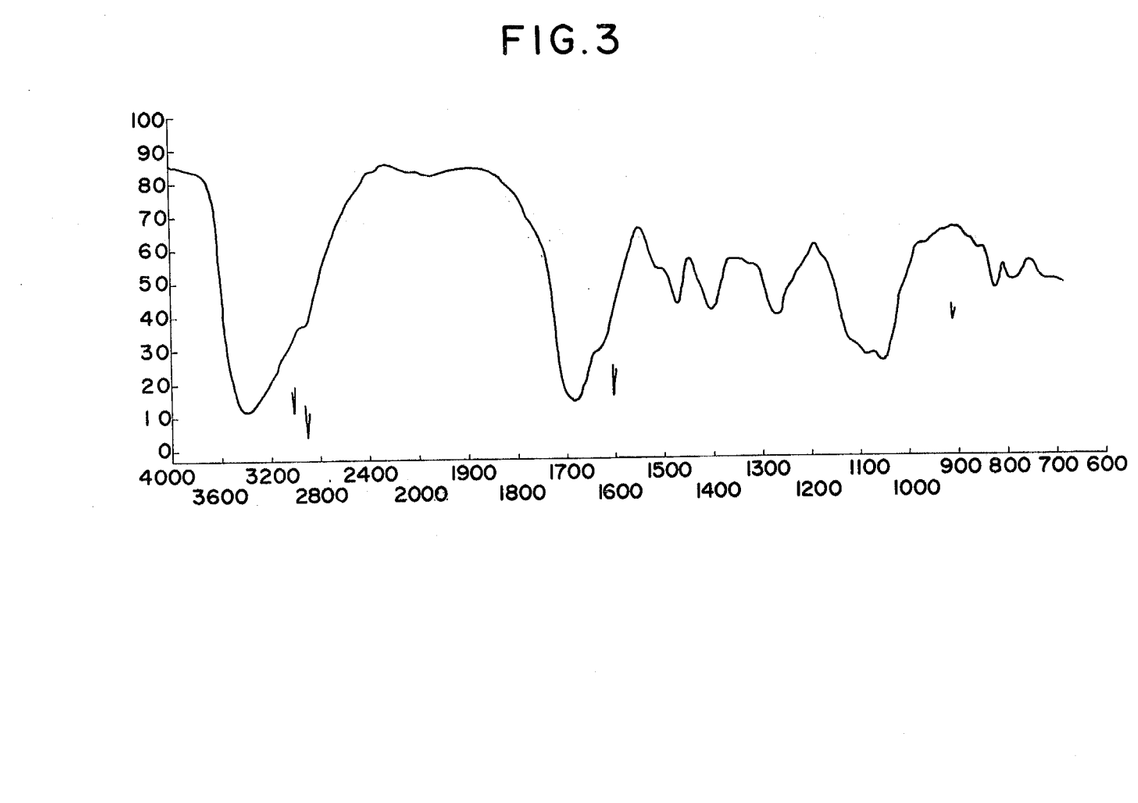
FIG. 3 shows a curve of the infrared absorption specturm of a sample of the hydrobromide of tunicamine derivative C pelleted in a KBr tablet.
Figure 4:
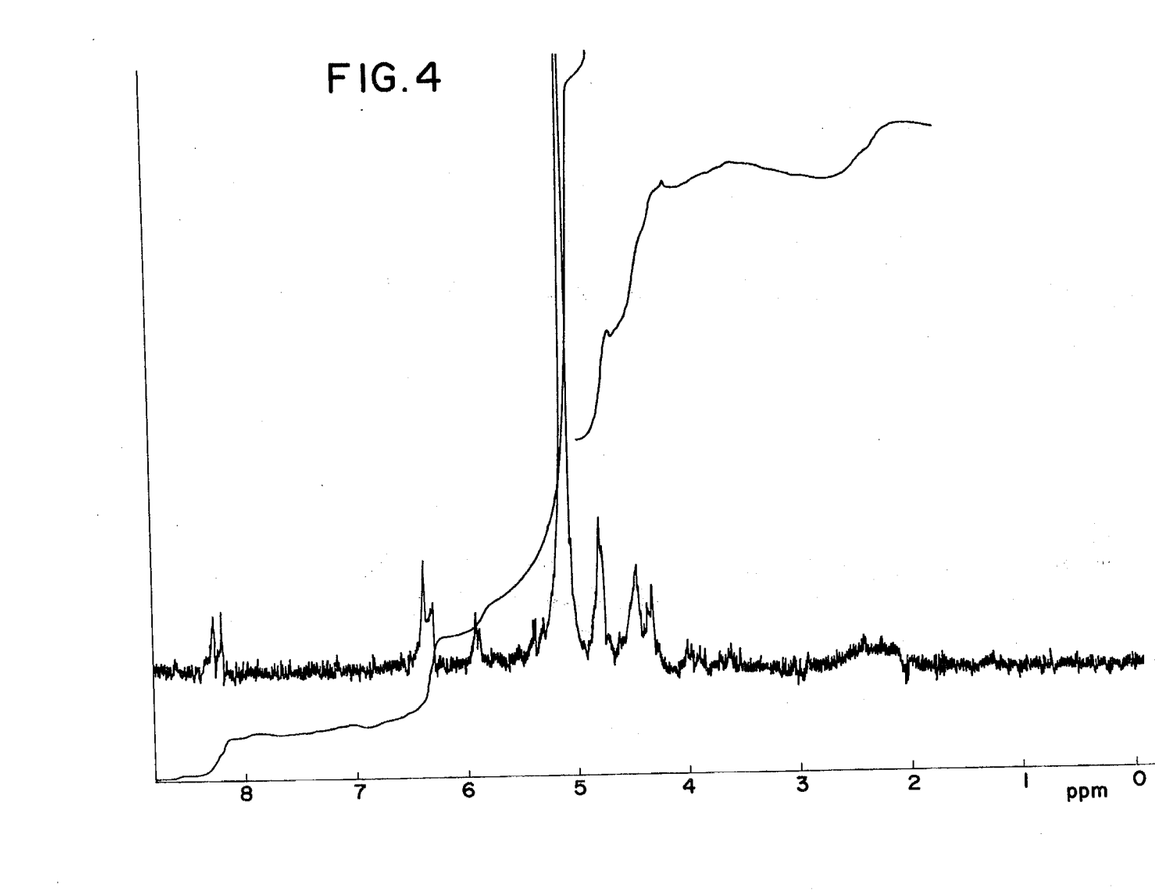
FIG. 4 shows a curve of the nuclear magnetic resonance spectrum of a sample of tunicamine derivative C in deutero-water.

Some biological activities of the tunicamine derivatives according to this invention were tested as follows:

Antiviral activity of tunicamine derivative B against Newcastle disease virus (NDV) was determined by the agar-diffusion plaque-inhibition method. The result is shown as percent inhibition in the following Table.

| Concentration (mcg/ml) | Anti-NDV activity (% inhibition) |
|---|---|
| 1500 | 30–50 |
| 2000 | 60–70 |
| 3000 | 70–80 |

Inhibitory activity of tunicamine derivative C against coccidiosis was tested in the following manner.

Primary chicks newly-hatched out were raised with a standard assorted feed for chicks containing no tunicamine derivative C for the first 7 days and on and after the 8th day with the same feed as above but containing a 100 ppm or 200 ppm concentration of tunicamine derivative C. On the 8th day from the hatch the body weight of the chicks was taken and they were divided into test groups of five chicks per group so as to balance the weight distribution for respective groups. On the 9th day, each chick was orally inoculated with $5.0 \times 10^4$ matured oocysts of Eimeria tenella. Assessment was made by observation and determination of the presence of hemaferia on the 4, 5, 6, 7 and 8 from day inoculation; percent of survivals on the 8th day and the extend of symptoms on the 8th day from the inoculation were then evaluated. The results are shown in the following Table.

| Test group | Compound tested | Concentration (ppm) | Presence of hemaferia[1] | | | | | Percent of survivals (%) | Relative[2] increase in body-weight (%) | Extent of[3] symptoms |
|---|---|---|---|---|---|---|---|---|---|---|
| | | | 4th | 5th | 6th | 7th | 8th | | | |
| 1 | Tunicamine derivative C | 100 | − | − | ± | ± | + | 100 | 96 | ++ |
| 2 | Tunicamine derivative C | 200 | − | − | − | − | − | 100 | 102 | − |
| 3 | Control, inoculated, but not treated | − | + | +++ | ++++ | ++++ | ++++ | 80 | 39 | ++++ |
| 4 | Control, not inoculated and not treated | − | − | − | − | − | − | 100 | 100 | − |

[1]Presence of hemaferia is expressed as follows:
− Not existing
± Something like hemaferia is likely to exist
+ A little hemaferia exists
++ Distinct hemaferiae exist in places
+++ Distinct hemaferiae exist almost over the whole
++++ The whole are hemaferiae

[2]Relative increase in body weight (%) is calculated as follows:
$$\frac{\text{(Increase in body-weight in the treated group)}}{\text{(Increase in body-weight in the control group)}} \times 100$$

[3]Extent of symptoms is shown by observing the symptoms occurring in the caecum with the naked eyes, classifying the extent of the symptom into five grades and obtaining an average grade in each test group. The indication is as follows:
− Quite normal
+ The shape of the caecum is normal, but partial, slight swelling is observed on the mucosa of the caecum
++ A small number of white spots of necrosis and blood spots are observed, but no bleeding is found in the caecum
+++ Distinct atrophic deformation of the caecum is observed. The contents of caecum are coagulated blood in greyish white cheese appearance.
++++ More remarkable atrophic deformation of caecum is observed. Others are similar to +++

Acute toxicity of tunicamine derivatives B and C was assessed by intraperitoneal injection to six male mice per group for each concentration, when all the six mice survived at 200 mg/kg concentration in both the derivatives B and C.

The tunicamine derivatives of formula (I) according to this invention may be prepared either by a fermentation process similar to that used for the preparation of tunicamycin or by hydrolysis of tunicamycin under acidic conditions.

According to another aspect of this invention, therefore, there is provided a process for the preparation of tunicamine derivatives the formula (I) which comprises cultivating a tunicamine derivative-producing strain of the genus Streptomyces under aerobic conditions in a suitable culture medium containing assimilable carbon and nitrogen sources for a period of time sufficient to produce and accumulate the tunicamine derivatives in said medium and recovering the tunicamine derivatives from the culture in a manner known per se.

For the preparation of tunicamine derivatives according to this invention, a strain of the genus Streptomyces may be used so far as this strain produces the tunicamine derivatives. One typical strain of the genus Streptomyces which we actually used is Streptomyces lysosuperificus which is known and used as tunicamycin-producing strain as disclosed in the abovementioned Japanese patent Publication. This strain was depositioned on Aug. 13, 1970 in a Japanese authorized depository, "Fermentation Research Institute, Agency of Industrial Science and Technology", Inage, Chiba-City, Japan, under deposit number FERM-P-653 and also on May 5, 1978 in the American Type Culture Collection, Rockville, Maryland under ATCC nunber 31396.

*Streptomyces lysosuperficus* has the following microbiological characteristics:

I. Morphological observation (1) Aerial mycelium: aerial mycelia produce abundantly on glucose-asparagine agar and on starch synthetic agar. Conidiophores are of straight form and form a tuft or cluster. Spirals are rarely observed.

(2) Conidiospore: conidiospores are of elliptical or cylindrical shape and have a size of 0.5−0.8×0.8−1.1 microns. The surface structure of the spores is smooth.

II. Characteristics of the growth on various culture media

| Culture medium | Growth | Aerial mycelium | Soluble pigment |
| --- | --- | --- | --- |
| Sucrose Czapek's agar | Poor growth, colorless to cream | Pale rose to lavender | None |
| Glycerin Czapek's agar | Pale brown with pale purple tinge | Scant, white to whity rose | Very faint purple |
| Glucose-asparagine agar (Krainsky) | Cream to pale yellow | Abundant, grey with rose tinge to dark rose | None |
| Glucose-asparagine agar (Ushinsky) | Good, brownish yellow | Abundant, grey with rose tinge | None |
| Calcium malate agar | Poor growth, colorless to cream | Very scant, white | None |
| Glycerin-calcium malate agar | Poor growth, colorless | None or very scant, white | None |
| Nutrient agar | Brownish yellow | None | None |
| Starch synthetic agar | Good, light orange | Abundant, grey with rose tinge, with formation of grey to olive patches | Light rose to orange, turning to bluish purple at alkaline pH |
| Plain agar | Brownish yellow | None | None |
| Glucose bouillon agar | Dark rose, with wrinkles, turning to purple at alkaline pH | None | None |
| Tyrosine agar | Brown | Grey | None |
| Peptone-glucose agar | Good, dark rose to brown | None or scant, grey | None or pale brown |
| Glucose Czapek's solution | Mainly surface growth, colorless to cream | None | None |
| Potato plug | With formation of fine wrinkles, red | None | None |
| Carrot plug | With somewhat upheaved surface, pale brown with reddish tinge | None or very scanty white | None |
| Bacto-nitrate froth medium | Surface growth, with some bottom growth | None | None |
| Skimmed milk | Ring growth, pale brown | None | Pale brown |
| Litmus milk | Ring growth, pale brown | None | Pale brown |
| Cellulose | No growth | None | None |
| Egg | Brown with purple tinge | None | None |
| Loeffler's coagulated serum | Blackish brown | None | None |
| Gelatine (20° C.) | Pale brown | White | Blacky brown in the periphery of the growth |
| Peptone-iron | Dark brown to black | None | Brown |

Note: The incubation temperature was 28° C. unless otherwise stated.

III. Physiological properties

Optimum growth conditions:

Aerobic; On starch-synthetic agar, optimum conditions for good growth were estimated to be 25°–34° C. and a pH of 6–8.

Growable conditions:

Aerobic; temperature range 15°–40° C.; pH range 4.5–9.5.

Production of tyrosinase: Negative
Production of hydrogen sulfide: Positive
Hydrolysis of starch: Positive
Reduction of nitrate: Positive
Peptonization of skimmed milk: Negative
Coagulation of skimmed milk: Negative
Dissolution of Loeffler's coagulated serum: Negative
Liquefaction of gelatine: Negative

IV. Utilization of carbon sources

1. Utilized: glucose, galactose, fructose, maltose, dextrin, starch, glycerin, sodium citrate, sodium succinate, salicin, mannose.
2. Doubtful: rhamnose, xylose, saccharose, inulin.
3. Not utilized: arabinose, lactose, raffinose, dulcitol, sorbitol, mannitol, inositol, sodium acetate, cellulose.

The aforesaid microbiological characteristics of the strain, *Streptomyces lysosuperificus* may be summarized as follows:

Conidiophore is straight and forms a tuft or cluster. Spiral hyphase are rarely observed. The surface structure of the conidiospore is smooth. On synthetic culture media, pale yellow to orange colored growth is observed with the formation of greyish rose to dark rose colored aerial mycelia. No formation of soluble pigment is observed in most cases, but on starch-synthetic agar medium, the formation of soluble pigment of rose color is observed which changes into purple color at an alkaline pH. On organic culture media, brown to red colored growth is observed and, in particular, growth with remarkable red color is observed on a potato plug. The formation of aerial mycelia is poor. The formation of soluble pigment is also poor, that is only blackish brown color is observed on gelatine medium and peptone-iron medium and the formation of melanin pigment is not distinct.

The cultivation of spores or mycelia of Streptomyces lysosuperificus in a culture medium under aerobic conditions in a known manner as disclosed in Japanese Patent Publication No. 29156/73, we have found, produces not only tunicamycin but also the tunicamine derivatives of formula (I), that is a mixture of tunicamine derivatives B and C. The separation of tunicamycin and tunicamine dericatives B and C from the culture broth and the isolation of tunicamycin, tunicamine derivatives B and C from one another may be achieved generally by utilizing any of the methods known per se which are usually available for the recovery, purification and isolation of known antibiotics and similar substances, the details of which are given later.

The cultivation step may be conducted in a known manner as used for the cultivation of actinomycetes. Thus, an amount of spores or mycelia of a tunicamine derivative-producing strain is inoculated to a suitable culture medium comprising nutrient sources and is then incubated under aerobic conditions, preferably under submerged aerobic conditions, until a sufficient amount of the tunicamine derivatives of formula (I) is produced in the culture medium. As the nutrient sources, any of the known nutrients which have usually been used in the cultivation of ordinary actinomycetes may be used. For example, commercially available soybean meal, peanut powder, cotton seed powder, dried yeast, peptone, meat extract, casein, corn steep liquor, N-Z amine, ammonium nitrate, ammonium sulfate and others may be useful as nitrogen sources. Similarly, commercially available carbohydrates such as glucose, starch, glycerol, maltose, dextrin, saccharose, lactose, molasses and others as well as fats and oils may be useful as carbon sources. In addition thereto, inorganic salts such as sodium chloride, calcium carbonate, potassium chloride, magnesium sulfate, magnesium chloride, cobalt dichloride and sodium phosphate may be used in the culture medium. If necessary, organic and inorganic materials which aid the growth of the tunicamine derivative-producing strain and promote the production of tunicamine derivatives may also be included in the medium.

Liquid cultivation, particularly under submerged aerobic conditions, is preferred for large scale operations, although solid cultivation may also be used. The cultivation is usually conducted at a temperature of 20°-34° C. under aerobic conditions. The most preferred temperature for the cultivation is 26°-28° C. The cultivation is continued for a period of time sufficient to produce and accumulate a sufficient amount of the tunicamine derivatives desired in the culture medium. Usually, a period of 2-4 days will be suitable for this purpose.

The separation of tunicamine derivatives from the culture medium and the isolation of tunicamine derivatives B and C from each other may be achieved by utilizing any one combination of methods known per se which are usually used for the recovery, purification and isolation of known antibiotics or other valuables from culture media.

PREFERRED EMBODIMENTS OF THE INVENTION

By way of example, the cultivation of Streptomyces lysosuperificus identified as ATCC No. 31396 and the recovery of the desired tunicamine derivatives from the culture medium are now explained.

In the cultivation of spores or mycelia of Streptomyces lysosuperificus conducted in a culture medium under aerobic conditions in a known manner as disclosed in Japanese Patent Publication No. 29156/73 referred to above, we have now found that the new, useful tunicamine derivatives of formula (I) are produced and accumulated in the culture medium in addition to tunicamycin which was recovered and confirmed as new antibiotic compound in the above-mentioned publication. All these valuables are found in both the solid phase, i.e. mycelium mass, and the liquid phase, i.e. the culture broth, of the culture medium. Thus, the culture medium may be filtered to separate it into the solid phase and the liquid phase. The solid phase, i.e. the mycelium cake, may then be extracted with a suitable organic solvent such as methanol or acetone to transfer the valuables into the solvent phase, and the liquid phase, i.e. the culture broth filtrate, may then be extracted with a suitable organic solvent such as n-butanol at an acidic or neutral pH to transfer the valuables into the solvent phase. In either case, the solvent phase may be subjected to distillation to remove the solvent therefrom and the residue containing the valuables may be subjected to chromatographic separation such as by column chromatography on a suitable adsorbent such as silica gel, alumina and Frorigil (activated magnesium silicate) to isolate each of these valuables. Various solvent systems may be used as the eluent in the column chromatography. By way of illustration, the elution of the valuables absorbed on silica gel by column chromatography was carried out using as eluents, in order, a solvent system of n-butanol, acetic acid, water and butyl acetate with a volume ratio of 4:1:1:6 (solvent A), the same solvent system with a volume ratio of 4:1:1:2 (solvent B) and the same solvent system with a volume ratio of 4:1:1:1 (solvent C), where impurities were eluted with the solvent A, tunicamine derivative B was eluted with the solvent B and tunicamine derivative C with the solvent C. Tunicamycin was eluted between the elution of tunicamine derivative B and that of tunicamine derivative C, that is, most of tunicamycin were eluted by solvent C and a part thereof by solvent B.

According to a further aspect of this invention, we provide a process for the preparation of tunicamine derivatives of formula (I) which comprises subjecting tunicamycin to acid hydrolysis and recovering the tunicamine derivatives thus formed from the hydrolyzed mixture in a manner known per se.

The acid hydrolysis may be carried out in a manner known per se, for example by heating tunicamycin in dilute, e.g. 3 N, hydrochloric acid under reflux for a period of time sufficient to cause the hydrolysis of tunicamycin, e.g. for 3 hours.

The isolation of the tunicamine derivatives from the hydrolyzed mixture may be achieved by a method or methods known per se. Thus, the hydrolyzed mixture may be extracted with a suitable organic solvent, e.g. n-butanol, and the extract may be subjected to a chromatographic separation, e.g. by a column chromatography on silica gel with the elution using, e.g. methanol, as eluent. The tunicamine derivative B may be isolated from the methanol eluate as a white crystalline precipitate on addition of an amount of water. The aqueous raffinate from the n-butanol extraction may be neutralized with a weakly basic anion-exchange resin, e.g. Amberlite IRA-94 (OH-form), then adsorbed on a weakly acidic cation-exchange resin, e.g. Amberlite IRC-50 ($NH_4$-form), eluted with an aqueous, e.g. 0.1 N, ammonia and then chromatographed with a strongly basic anion-exchange resin, e.g. Diaion PA 306 (Br-form).

The tunicamine derivatives B and C as prepared and isolated by either of the above-mentioned fermentation and acid hydrolysis processes have been identified to have the chemical structures of the formula (I) above by comparing analytical data thereof such as elemental analysis, specific rotation, melting point, ultraviolet spectrometry, infrared spectrometry, nuclear magnetic resonance spectrometry and mass spectrometry.

The following Examples further illustrate, but does not limit, this invention.

EXAMPLE 1

(a) The strain, *Streptomyces lysosuperificus* identified under ATCC No. 31396 was inoculated to 20 l of a liquid culture medium containing 2.2% glycerin, 2.0% corn gluten meal, 1.8% cotton seed meal, 0.3% calcium carbonate, 0.05% magnesium sulfate, 0.02% cobalt dichloride, 3.0% dipotassium hydrogenphosphate and 1.5% potassium dihydrogenphosphate at pH 6.8 and cultivated at 28° C. under aeration (20 l/min.) with stirring at 300 rpm. The residual glycerin content of the medium was determined to be 0.1% after the cultivation of 4 days, at which the cultivation was stopped and the cultured mixture was filtered to separate it into a mycelium cake and a culture broth filtrate.

The filtrate (18 l) was adjusted to pH 4.5 with the addition of 6 N hydrochloric acid and then stirred with 10 l of n-butanol added to transfer tunicamine derivative B and most of the tunicamycin into the n-butanol phase. The n-butanol layer which separated on standing was collected, concentrated to the volume of 0.6 l and dehydrated on anhydrous sodium sulfate, to which acetone (3 l) was then added to deposit a precipitate.

The mycelium cake (wet weight: 2.1 kg) was extracted with methanol (2 l×2) and the combined extract was subjected to distillation under vacuum to remove the methanol, leaving 300 ml of concentrate. The concentrate was adjusted to pH 4.5 and extracted with 1600 ml of n-butanol to transfer the tunicamine derivative B and the tunicamycin into the n-butanol phase. The n-butanol layer which separated on standing was concentrated to the volume of 0.6 l and dehydrated on anhydrous sodium sulfate, to which acetone (3 l) was then added to cause precipitation.

The precipitates both from the filtrate and from the cake as above were combined together and dried to give 14.1 g of crude powder containing tunicamine derivative B and tunicamycin in the purity of about 2% and 6%, respectively.

(b) For the recovery of tunicamine derivative C, the aqueous raffinate from the n-butanol extraction step was passed through a column of 2 l of a weakly basic anion-exchange resin, Amberlite IRA 94 (acetate form), with the subsequent washing of the column with 3 l of water. The aqueous raffinate passed through the column and the washings were combined together and the mixture was passed through a column of 2 l of a weakly acidic cation-exchange resin, Amberlite IRA-50 ($NH_4$-form), to adsorb the active substances thereon. After the washing with water and elution with 0.1 N ammonium hydroxide solution, the eluate fractions were tested by means of silica gel thin layer chromatography (using Silica gel G manufactured by Merck Co. and 4:1:1 by volume mixture of n-butanol, acetic acid and water as developer), on the basis of which fractions containing tunicamine derivative C were collected and concentrated in vacuo to give 2.5 g of crude powder containing tunicamine derivative C in a purity of about 5%.

EXAMPLE 2

(a) Five grams of the crude powder containing tunicamine derivative B and tunicamycin obtained in Example 1 (a) were taken together with n-butanol and silica gel (Merck Si-60) in the form of a paste and treated by column chromatography using a 500 ml silica gel column using a mixture of n-butanol, acetic acid, water and butyl acetate (4:1:1:2 by volume) as eluent. The eluate fractions were tested by means of thin layer chromatography, on the basis of which fractions containing tunicamine derivative B were collected and concentrated in vacuo and dried. The dried concentrate was again treated by column chromatography using a 100 ml silica gel column with the elution using the same solvent system as above, affording 42 mg of tunicamine derivative B. A part of tunicamycin was eluted after the elution of tunicamine derivative B.

(b) One gram of the crude powder containing tunicamine derivative C obtained in Example 1 (b) was treated by column chromatography on a 500 ml silica gel column which had been impregnated with a solvent mixture comprising n-butanol, acetic acid, water and butyl acetate (4:1:1:4 by volume). The elution was effected using the same solvent system as above with a different ratio (4:1:1:1 by volume) as eluent. The eluate fractions were analyzed by a thin layer chromatography, on the basis of which fractions containing tunicamine derivative C were collected and concentrated to dryness in vacuo, affording 17 mg of tunicamine derivative C. A part of tunicamycin was eluted before the elution of tunicamine derivative C.

(c) Fractions containing tunicamycin obtained in both the steps (a) and (b) above were collected and rechromatographed on a 200 ml silica gel column using the same solvent system as above, affording 180 mg of tunicamycin.

Both the tunicamine derivatives B and C obtained as above in a pure state were identified by thin layer chromatography, nuclear magnetic resonance spectrum, melting point and elemental analysis to be the same materials as the standard samples.

EXAMPLE 3

Ten grams of tunicamycin in 70% purity were dissolved in 500 ml of 3 N hydrochloric acid and the solution was heated under reflux with stirring for 3 hours to cause hydrolysis of tunicamycin. The resulting mixture was extracted twice with 500 ml each of n-butanol. The combined n-butanol extract was concentrated in vacuo and the concentrate was treated by column chromatography on a 200 ml silica gel column (Si-60 manufactured by Merck Co.) which had been impregnated with a solvent system comprising n-butanol, acetic acid, water and butyl acetate (4:1:1:8 by volume). After elution with 400 ml of the same solvent system as above for the removal of impurities, elution of the desired compound, tunicamine derivative B, was effected using the same solvent system as above with a different ratio (4:1:1:4). The eluate fractions thus separated were analyzed by silica gel thin layer chromatography (using Silica gel G and a 4:1:1 by volume mixture of n-butanol, acetic acid and water as developer), on the basis of which fractions containing tunicamine derivative B were collected and concentrated to dryness in vacuo, affording 190 mg of crude powder containing tunicamine derivative B in 75% purity. The crude powder was dissolved in 10 ml of methanol and the solution was filtered to remove insoluble matter. The clear solution, after addition of 30 ml of water thereto, was allowed to stand under cooling, during which a crystalline mass was deposited from the solution, separated by filtration and dried to yield 104 mg of crystalline powder. This was identified by the above-mentioned analyses to be tunicamine derivative B.

EXAMPLE 4

The aqueous raffinate remaining after the extraction with n-butanol of the hydrolyzed mixture in Example 3 was concentrated in vacuo, while water was added thereto, to remove the hydrochloric acid and to give a final volume of 20 ml of the concentrate. The concentrate was charged into a column of 200 ml of an ion-exchange resin, Amberlite IRC-50 ($NH_4$-form), washed with 1 l of water and eluted with 0.1 N aqueous ammonia solution. Fractions eluted between 400 ml and 600 ml of the eluate volume totally measured from the beginning were collected and adjusted to pH 7.0 and concentrated to dryness in vacuo, yielding 810 mg of crude powder containing tunicamine derivative C.

The crude powder was taken together with n-butanol and silica gel (Si-60 manufactured by Merck Co.) in the form of a paste and was charged into a silica gel column (140 ml) which had been impregnated with a solvent system comprising n-butanol, acetic acid, water and butyl acetate (4:1:2:4 by volume). After the previous elution with 800ml of the same solvent system as above, the elution was effected using 1.6 l of the same solvent system as above with a different ratio (4:1:1:4 by volume). Fractions eluted between 480 ml and 580 ml of the eluate volume totally measured from the beginning, which were analyzed by thin layer chromatography to contain tunicamine derivative C, were collected and concentrated to dryness in vacuo, yielding 380 mg of crude powder containing tunicamine derivative C. The crude powder was dissolved in 20 ml of water and the solution was charged into a 100 ml column of a strongly basic anion-exchange resin, Diaion PA 306 (Br-form), and eluted with water. The eluate fractions were analyzed by silica gel thin layer chromatography (Silica gel G manufactured by Merck Co. and a solvent comprising 2:1:1 by volume of n-butanol, acetic acid and water), on the basis of which fractions containing tunicamine derivative C were collected, concentrated and freeze-dried, yielding 335 mg of white powder. This was identified by elemental analysis, infrared absorption spectrum, ultraviolet absorption spectrum, melting point, nuclear magnetic resonance spectrum and mass spectrometry to be the same compound as the standard sample.

What we claim is:

1. A tunicamine derivative of the formula:

wherein R represents hydrogen or a fatty acid residue of the formula $(CH_3)_2CH(CH_2)_nCH=CHCO$—where n represents an integer of 8 to 11 inclusive.

2. A tunicamine derivative according to claim 1 which is designated as tunicamine derivative C and which is of the formula:

3. A tunicamine derivative according to claim 1 which is in the form of a mixture designated as tunicamine derivative B and which is of the formula:

wherein n represents integers of 8 to 11 inclusive.

* * * * *